US00PP19522P2

(12) United States Plant Patent
Iwaki et al.

(10) Patent No.: US PP19,522 P2
(45) Date of Patent: Dec. 2, 2008

(54) ***TORENIA* PLANT NAMED 'SUNRENICOBAIO'**

(50) Latin Name: ***Torenia* sp.**
Varietal Denomination: Sunrenicobaio

(75) Inventors: Kazunari Iwaki, Kanagawa (JP); Takeshi Kanaya, Shiga (JP); Kenichi Suzuki, Osaka (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/998,806

(22) Filed: Nov. 30, 2007

(51) Int. Cl.
*A01H 5/00* (2006.01)

(52) U.S. Cl. ..... Plt./487

(58) Field of Classification Search ..... Plt./353
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Torenia* plant named 'Sunrenicobaio', characterized by its compact and mounding to trailing plant habit; freely branching habit; freely flowering habit; long flowering period; violet-colored flowers with white-colored centers; and good garden performance.

1 Drawing Sheet

Botanical designation: *Torenia* sp.
Cultivar denomination: 'Sunrenicobaio'.

BACKGROUND OF THE INVENTION

The present invention relates to a new and distinct cultivar of *Torenia,* botanically known as *Torenia* sp. and hereinafter referred to by the name 'Sunrenicobaio'.

The new *Torenia* is a whole plant mutation of a proprietary selection of *Torenia* sp. identified as code number TH1, not patented. The new *Torenia* was discovered and selected by the Inventors as a single plant in a controlled greenhouse environment in Higashiomi, Shiga, Japan in March, 2004.

Asexual reproduction of the new *Torenia* by vegetative cuttings in a controlled environment in Higashiomi, Shiga, Japan since October, 2004, has shown that the unique features of this new *Torenia* are stable and reproduced true to type in successive generations.

SUMMARY OF THE INVENTION

The cultivar Sunrenicobaio has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunrenicobaio'. These characteristics in combination distinguish 'Sunrenicobaio' as a new and distinct cultivar of *Torenia:*

1. Compact and mounding to trailing plant habit.
2. Freely branching habit.
3. Freely flowering habit.
4. Long flowering period.
5. Violet-colored flowers with white-colored centers.
6. Good garden performance.

Compared to plants of the parent selection, plants of the new *Torenia* are smaller and have narrower leaves. In addition, plants of the new *Torenia* and the parent selection differ in flower color as plants of the parent selection have violet-colored flowers with violet-colored centers.

Plants of the new *Torenia* can also be compared to plants of the cultivar Sunrenibu, disclosed in U.S. Plant Pat. No. 10,119. In side-by-side comparisons conducted in Higashiomi, Shiga, Japan, plants of the new *Torenia* and the cultivar Sunrenibu differed in the following characteristics:

1. Plants of the new *Torenia* were smaller than plants of the cultivar Sunrenibu.
2. Plants of the new *Torenia* had shorter internodes than plants of the cultivar Sunrenibu.
3. Plants of the new *Torenia* had longer leaves than plants of the cultivar Sunrenibu.
4. Plants of the new *Torenia* had larger flowers than plants of the cultivar Sunrenibu.
5. Plants of the new *Torenia* and the cultivar Sunrenibu differed in flower color.

BRIEF DESCRIPTION OF THE PHOTOGRAPHS

The accompanying colored photographs illustrate the overall appearance of the new *Torenia,* showing the colors as true as it is reasonably possible to obtain in colored reproductions of this type. Colors in the photographs may differ slightly from the color values cited in the detailed botanical description which accurately describe the colors of the new *Torenia.*

The photograph at the top of the sheet comprises a side perspective view of a typical flowering plant of 'Sunrenicobaio' grown in a container.

The photograph at the bottom of the sheet is a close-up view of typical flowers and leaves of 'Sunrenicobaio'.

DETAILED BOTANICAL DESCRIPTION

The aforementioned photographs and following observations, measurements and values describe plants grown in Higashiomi, Shiga, Japan, under commercial practice during the winter in a polyethylene-covered greenhouse with day temperatures averaging 20° C. and night temperatures averaged 10° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Torenia* sp. cultivar Sunrenicobaio.

Parentage: Whole plant mutation of a proprietary selection of *Torenia* sp. identified as code number TH1, not patented.

Propagation:

*Type.*—By vegetative cuttings.

*Time to initiate roots.*—About one week at 20° C. to 25° C.

*Time to produce a rooted young plant roots.*—About three to four weeks at 20° C. to 25° C.

*Root description.*—Fine, fibrous and fleshy; pale brown in color.

*Rooting habit.*—Freely branching.

Plant description:

*Plant form/habit.*—Compact and mounded to trailing plant habit; outwardly spreading; vigorous growth habit. Freely branching habit; pinching enhances branching.

*Plant height.*—About 9 cm.

*Plant width (spread).*—About 63 cm.

*Lateral branches.*—Length: About 33.4 cm. Diameter: About 2 mm. Internode length: About 2.8 cm. Aspect: Decumbent. Texture: Smooth, glabrous. Color: 144A.

Foliage description:

*Arrangement.*—Opposite, simple.

*Length.*—About 2.8 cm.

*Width.*—About 1.6 cm.

*Shape.*—Ovate.

*Apex.*—Acute.

*Base.*—Cordate.

*Margin.*—Serrate.

*Texture, upper and lower surfaces.*—Pubescent.

*Venation pattern.*—Pinnate; reticulate.

*Color.*—Developing leaves, upper surface: 144A. Developing leaves, lower surface: 144C. Fully expanded leaves, upper surface: 137B; venation, 144A. Fully expanded leaves, lower surface: 146B; venation, 144A.

*Petiole.*—Length: About 4.8 mm. Diameter: About 0.9 mm. Texture, upper and lower surfaces: Smooth, glabrous. Color, upper and lower surfaces: 144A.

Flower description:

*Flower type/habit.*—Single flowers borne in upper leaf axils; corolla bilabiate and calyx tubular; flowers face obliquely upright. Freely flowering habit with about 50 open flowers per plant.

*Fragrance.*—None detected.

*Natural flowering season.*—Long flowering period; continuously flowering from early summer to late autumn in Japan. Flowers not persistent.

*Postproduction longevity.*—Flowers last about four days on the plant.

*Flower buds.*—Height: About 1.6 cm. Diameter: About 6.9 mm. Shape: Lenticular. Color: 144B.

*Flower diameter.*—About 2.9 cm by 2.6 cm.

*Flower depth.*—About 3.4 cm.

*Throat diameter.*—About 1 cm.

*Tube diameter, base.*—About 4.5 mm.

*Tube length.*—About 1.9 cm.

*Petals.*—Quantity per flower: Typically four in a single whorl, fused; one upper, two lateral and one lower petal. Upper petal: Length: About 1.2 cm. Width: About 1.8 cm. Shape: Transversely elliptic with cuspidate apex. Margin: Undulating. Texture, upper and lower surfaces: Smooth, glabrous; velvety. Color: Developing petals, upper surface: 83A; towards the throat, N155C. Developing petals, lower surface: 83B. Fully developed petals, upper surface: 83B; towards the throat, N155A. Fully developed petals, lower surface: N81A. Lateral petals: Length: About 1.5 cm. Width: About 1 cm. Shape: Elliptic with rounded apex. Margin: Entire. Texture, upper and lower surfaces: Smooth, glabrous; velvety. Color: Developing petals, upper surface: 83A. Developing petals, lower surface: 83B. Fully developed petals, upper surface: 83B. Fully developed petals, lower surface: N81A. Lower petal: Length: About 1 cm. Width: About 1.5 cm. Shape: Transversely elliptic with rounded apex. Margin: Entire. Texture, upper and lower surfaces: Smooth, glabrous; velvety. Color: Developing petals, upper surface: 83A; towards the throat, 85C. Developing petals, lower surface: 83B. Fully developed petals, upper surface: 83B; towards the throat, 85D. Fully developed petals, lower surface: N81A. Throat color: N81D; lines, N81A; at the base, 6B. Tube color: N81D.

*Sepals.*—Quantity per flower: Typically four fused in a single whorl. Length: About 1.4 cm. Width: About 6 mm. Shape: Oblong. Apex: Acute. Margin: Entire. Texture, upper and lower surfaces: Smooth, glabrous. Color, upper and lower surfaces: 144A.

*Peduncles.*—Length: About 2.2 cm. Diameter: About 1.8 mm. Texture: Smooth, glabrous. Color: 144A.

*Reproductive organs.*—Stamens: Quantity per flower: Typically four. Anther shape: Ellipsoidal. Anther size: About 3 mm by 0.5 mm. Anther color: Between N81B and 84C. Pollen amount: Scarce. Pollen color: Close to 10D. Pistils: Quantity per flower: One. Pistil length: About 2.1 cm. Stigma shape: Elliptic. Stigma color: 155C. Style color: 155C. Ovary color: 144A.

*Seed/fruit.*—Seed and fruit development have not been observed.

Disease/pest resistance: Plants of the new *Torenia* have not been noted to be resistant to pathogens and pests common to *Torenia*.

Garden performance: Plants of the new *Torenia* have been observed to have good garden performance and tolerate rain, wind and temperatures from about 5° C. to about 30° C.

It is claimed:

1. A new and distinct *Torenia* plant named 'Sunrenicobaio' as illustrated and described.

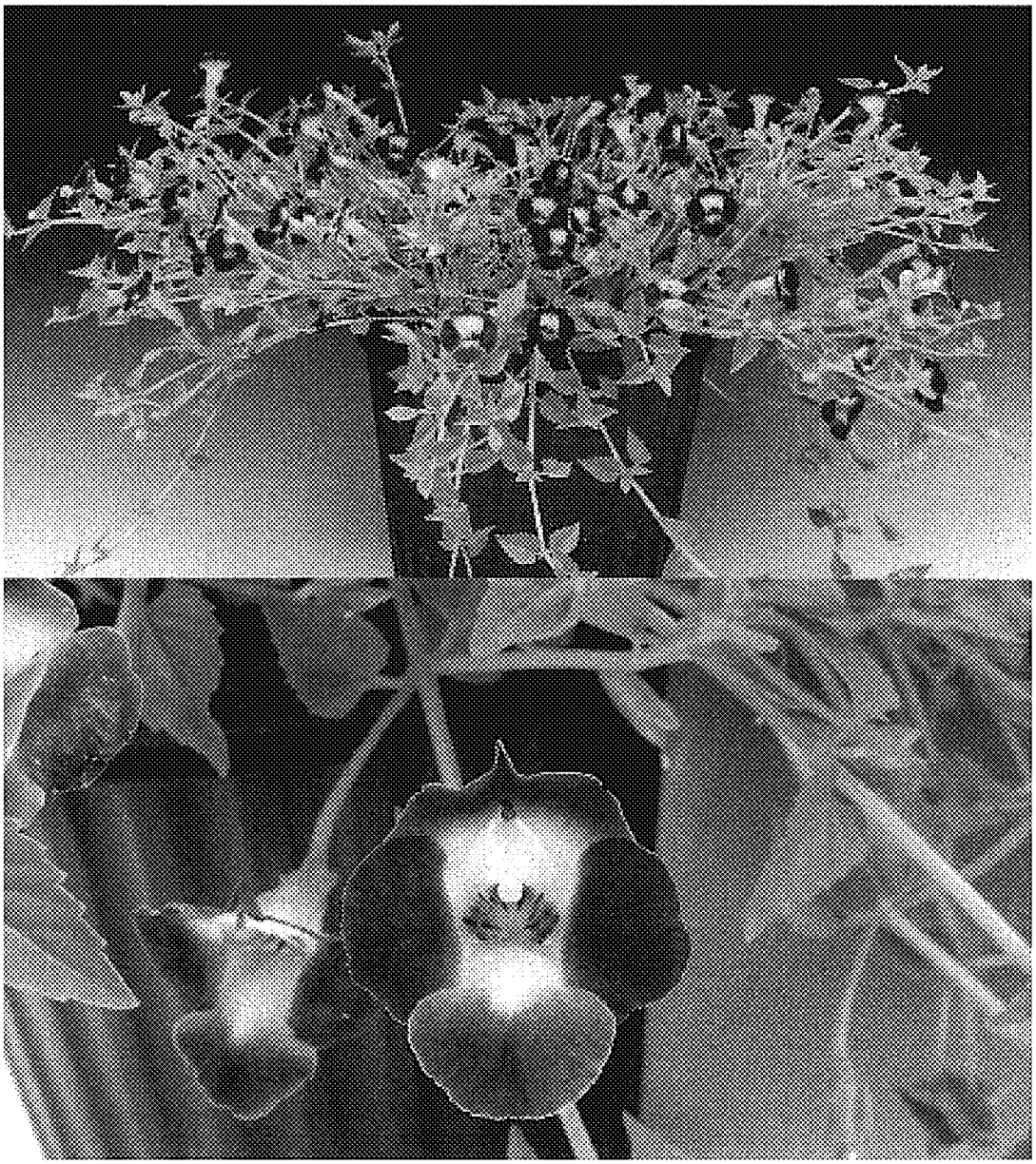

* * * * *